United States Patent [19]

Kummann

[11] Patent Number: 4,600,421
[45] Date of Patent: Jul. 15, 1986

[54] TWO-STAGE RECTIFICATION FOR THE SEPARATION OF HYDROCARBONS

[75] Inventor: Paul Kummann, Munich, Fed. Rep. of Germany

[73] Assignee: Linde Aktiengesellschaft, Wiesbaden, Fed. Rep. of Germany

[21] Appl. No.: 724,729

[22] Filed: Apr. 18, 1985

[30] Foreign Application Priority Data

Apr. 18, 1984 [DE] Fed. Rep. of Germany ....... 3414749

[51] Int. Cl.[4] ................................................. F25J 3/02
[52] U.S. Cl. .......................................... 62/25; 62/28; 62/29; 62/31; 62/34; 62/39
[58] Field of Search ................... 62/23, 24, 25, 27, 28, 62/29, 31, 32, 33, 34, 36, 38, 39, 42, 44

[56] References Cited

U.S. PATENT DOCUMENTS 4,455,158 6/1984 Vines et al. .............................. 62/28

Primary Examiner—Frank Sever
Attorney, Agent, or Firm—Millen & White

[57] ABSTRACT

To separate $C_{2+}$ or $C_{3+}$ hydrocarbons from hydrocarbon-containing gaseous mixtures by fractional condensation and rectification, the rectification is conducted in two columns, the second column being at a pressure at least 5 bar lower than the first. One of the condensates is subcooled before being passed, for purposes of peak cooling, to the upper zone of the high pressure column, substantial energy savings are realized.

22 Claims, 3 Drawing Figures

TWO-STAGE RECTIFICATION FOR THE SEPARATION OF HYDROCARBONS

BACKGROUND OF THE INVENTION

This invention relates to a system for the separation of $C_{2+}$ or $C_{3+}$ hydrocarbons from a hydrocarbon-containing raw gas under pressure, and in particular, wherein the raw gas is cooled and expanded and the resultant condensates are introduced into a rectification column wherein the $C_{2+}$ and $C_{3+}$ hydrocarbons are separated from the lower-boiling components.

Such a process, with the particular objective of obtaining $C_{2+}$ hydrocarbons, has been proposed in assignee's German Patent Application No. P 33 32 943.5 and corresponding U.S. application Ser. No. 650,016, filed Sept. 13, 1984, by Kummann et al, incorporated herein by reference. In this earlier patent application, the gas fed to the column and in some cases the gas withdrawn from the column as well, are subjected to different pressure stages which in turn facilitates heat transfer between separate streams. In a specific embodiment, a methane fraction is produced during the cooling of the crude gas by, in essence, cascade fractional condensation steps. This methane fraction is so depleted in $C_{2+}$ hydrocarbons that there is no need to introduce it into the rectifying stage. Accordingly, the fraction is not expanded to the rectification pressure and consequently, requires little or no compression before being discharged into a high-pressure methane pipeline.

SUMMARY OF THE INVENTION

An object of one aspect of the present invention is to provide an improved process of the type described above, especially from an energy viewpoint.

A still further object is to provide novel and patentable subcombination process aspects of the invention.

Upon further study of the specification and appended claims, further objects and advantages of this invention will become apparent to those skilled in the art.

To attain these objects, the rectification is conducted in at least two different pressure stages. The fractions produced during cooling and expansion of rhe raw gas are fed into a first rectification column operated under a higher pressure which yields (1) an overhead product containing components boiling lower than the $C_{2+}$ or $C_{3+}$ hydrocarbons, and (2) a bottoms fraction enriched in $C_{2+}$ or $C_{3+}$ hydrocarbons. The bottoms fraction, after expansion, is then fed into a second rectification column operated under a lower pressure where a $C_{2+}$ or $C_{3+}$ hydrocarbon fraction is obtained as the bottoms product. The overhead fraction obtained at the head of the second rectifying column is recycled, after compression, into the first rectifying column.

One advantage of the two-stage rectification is gained because the resultant overhead gas from the high pressure stage, i.e., the fraction free of $C_{2+}$ or $C_{3+}$, is at a higher pressure than when using a single-stage rectification. As a result, compression of this methane product fraction, which is ordinarily discharged into a high-pressure pipeline, can be omitted or at least reduced. This is the same sort of advantage as obtained in assignee's prior application Ser. No. 650,016; however, the present invention provides still additional advantages, as described below.

In a preferred embodiment of this invention, the overhead product from the second rectifying column is passed through an open refrigeration cycle, for which purpose it is heated, compressed, and after recooling, expanded into the first rectifying column. Instead of introducing the cooled overhead directly into the first rectifying column, a preferred technique is to recycle the cooled overhead either into the raw gas to be cooled, or into the raw gas removed of condensate. The open cycle also contains the low-boiling components dissolved in the bottoms product of the first rectifying column. In the process of this invention, it is now merely necessary to recompress this minor proportion of the low-boiling components, e.g., generally less than about 15%, especially less than 8% of the low boiling components which constitute mainly methane. For example, in a process for the separation of $C_{2+}$ hydrocarbons from a natural gas, the proportion of low-boiling components entering the second rectifying column amounts to only about 4% of the entire quantity of low-boiling components of the raw gas. The lower the amount that must be recompressed, the greater is the savings in energy. It is also important that the open refrigeration cycle can work at relatively high temperatures, e.g., about 210° to 300° K., especially 230° to 290° K., thus reducing the requirement for external refrigeration which otherwise would have to be made available by a closed multistage refrigeration cycle with a $C_3$ hydrocarbon as the coolant.

Since the largest portion of the low-boiling components is separated, in the process of this invention, at such a high pressure level that there is no need, or at least only a substantially reduced need, for compression energy, the energy obtained during the conventional turbine expansion of the cooled raw gas is available for uses other than for the conventional recompression of this fraction. The energy can be utilized, in particular, for providing such refrigeration as required in the process.

By operating the process according to this invention with two pressure stages, an additional advantage is gained whereby especially favorable temperature levels can be set in the second rectifying column operating under a relatively low pressure, whereby the refrigeration requirement of the process is further produced and/or can be covered in an especially advantageous way. Such especially favorable temperature levels lead to top and bottom temperatures of the second column between 230° and 300° K., thus leading to reboiling and intermediate reboiling by cooling of feedgas.

The most favorable process pressure to be maintained in the two rectifying columns depends in each case on the composition of the crude gas, the specific separation objectives, the desired discharge pressure for the gaseous, low-boiling components, and in some cases on additional process parameters. This pressure can be readily determined in an individual case by conventional engineering optimization calculations. In general, the pressure in the first rectifying column ranges between 20 and 40 bar, and in the second rectifying column between 8 and 25 bar, especially between 10 and 18 bar. The pressure difference between the two columns, in this connection, should be at least 5 bar and preferably about 5 to 20 bar. Although the process of this invention can also be operated at a lower pressure difference than 5 bar between the two columns, the positive effects attainable by this invention will be relatively small in such cases.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
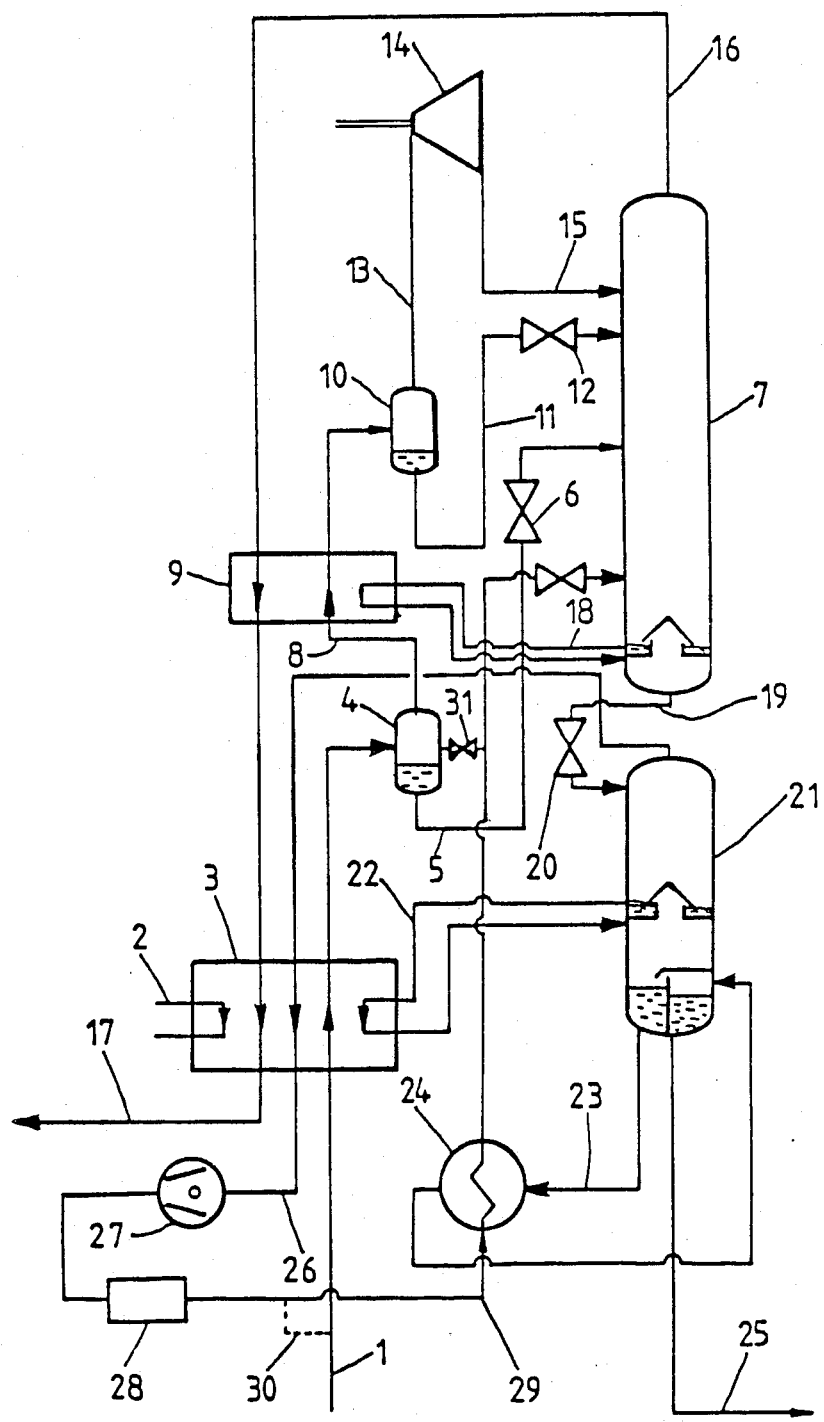
FIG. 1 is a schematic flowsheet of the separation of $C_{2+}$ hydrocarbons from a crude gas mixture.

In the embodiment shown in FIG. 1, a natural gas, containing 84.78 mol-% methane, 11.96 mol-% ethane and 3.26 mol-% propane, is supplied via conduit 1 under a pressure of 57 bar and at a temperature of 320° K. In an indirect heat exchanger 3 cooled by process streams to be heated and by a refrigeration cycle 2, the natural gas is cooled to 234° K. Components condensed during this step are separated in the downstream phase separator 4, withdrawn via a conduit 5, expanded in an expansion valve 6 to a pressure of 22 bar, and then fed into the lower zone of a first rectifying column 7 operated under this pressure.

The uncondensed proportion of the natural gas is discharged from phase separator 4 via conduit 8, cooled to 214° K. in heat exchanger 9 in indirect heat exchange against process streams to be heated, and conducted into another condensate phase separator 10. The components condensed out during the second cooling step, containing higher methane and ethane contents than in the condensate obtained in phase separator 4, are discharged via conduit 11, expanded in expansion valve 12 to the pressure of rectifying column 7, and fed into this column at a point corresponding to the equilibrium curve within the rectifying column 7.

The proportion of the natural gas not condensed in separator 10 is discharged via conduit 13, engine-expanded in a turbine 14 to the pressure of the rectifying column 7 and then introduced to the head of this column via conduit 15. The cooling achieved by the engine expansion step yields the peak cold at the head of the rectifying column 7 of 180.7° K.

The rectifying column 7, working under a pressure of 22 bar, operates in a temperature range of 180.7° K. at the head and 230° K. in the sump. A methane fraction is withdrawn at the head of the column containing 97.4 mol-% methane, 2.55 mol-% ethane and 0.05 mol-% propane. This gas is heated, via conduit 16, first in heat exchanger 9 and then in heat exchanger 3 against natural gas to be cooled, and is finally discharged into a product gas line 17 at ambient temperature under the pressure of the rectifying column 7 minus the small pressure losses occurring in the conduits.

Heat is provided in the sump region of the rectifying column 7 by conducting condensate via conduit 18 into heat exchanger 9 and, after partial heating, returning same into the sump region of rectifying column 7. The bottom product of column 7, containing only about 4% of the methane to be discharged into line 17, is removed via conduit 19 at 230° K., expanded to a pressure of 16 bar in valve 20, and introduced into the upper region of a second rectifying column 21 operated under this pressure.

Column 21, operated at a temperature range of between 230° K. at the head and 265° K. in the sump, separates the residual methane content, resulting from the sump product of rectifying column 7, from the $C_{2+}$ hydrocarbons to be obtained. The expansion taking place in valve 20 results in a partial degasification, e.g., 8 to 25% of the sump product of column 7.

The rectifying column 21 is subjected to intermediate heating and sump heating. For intermediate heating, liquid is withdrawn via conduit 22, partially heated in heat exchanger 3, and recycled into the rectifying column. For heating the sump, bottoms liquid is withdrawn via conduit 23, heated in a heat exchanger 24, and returned into the sump as a two phase mixture. The liquid fraction is about 75%, but largely depends on the extend of intermediate heating.

A bottoms product stream containing 0.7 mol-% methane, 74.65 mol-% ethane and 24.65 mol-% propane is removed from column 21 via conduit 25. A mixture of methane, ethane and propane obtained at the head of column 21 is removed via conduit 26 and circulated in an open cycle. After being heated in heat exchanger 3 against natural gas to be cooled, this fraction is compressed in a compressor 27, (the latter being drivable, for example, by turbine 14) recooled in a recooler 28 to ambient temperature, and then conducted via conduit 29 into heat exchanger 24 and finally into the lower zone of rectifying column 7. Alternatively, this fraction after, being cooled in recooler 28, can be conducted via conduit 30 into the natural gas before the latter is cooled in heat exchanger 3, or as still another alternative, the fraction after being cooled in heat exchanger 24, can be passed into the first separator 4 via conduit 31.

Figure 2:
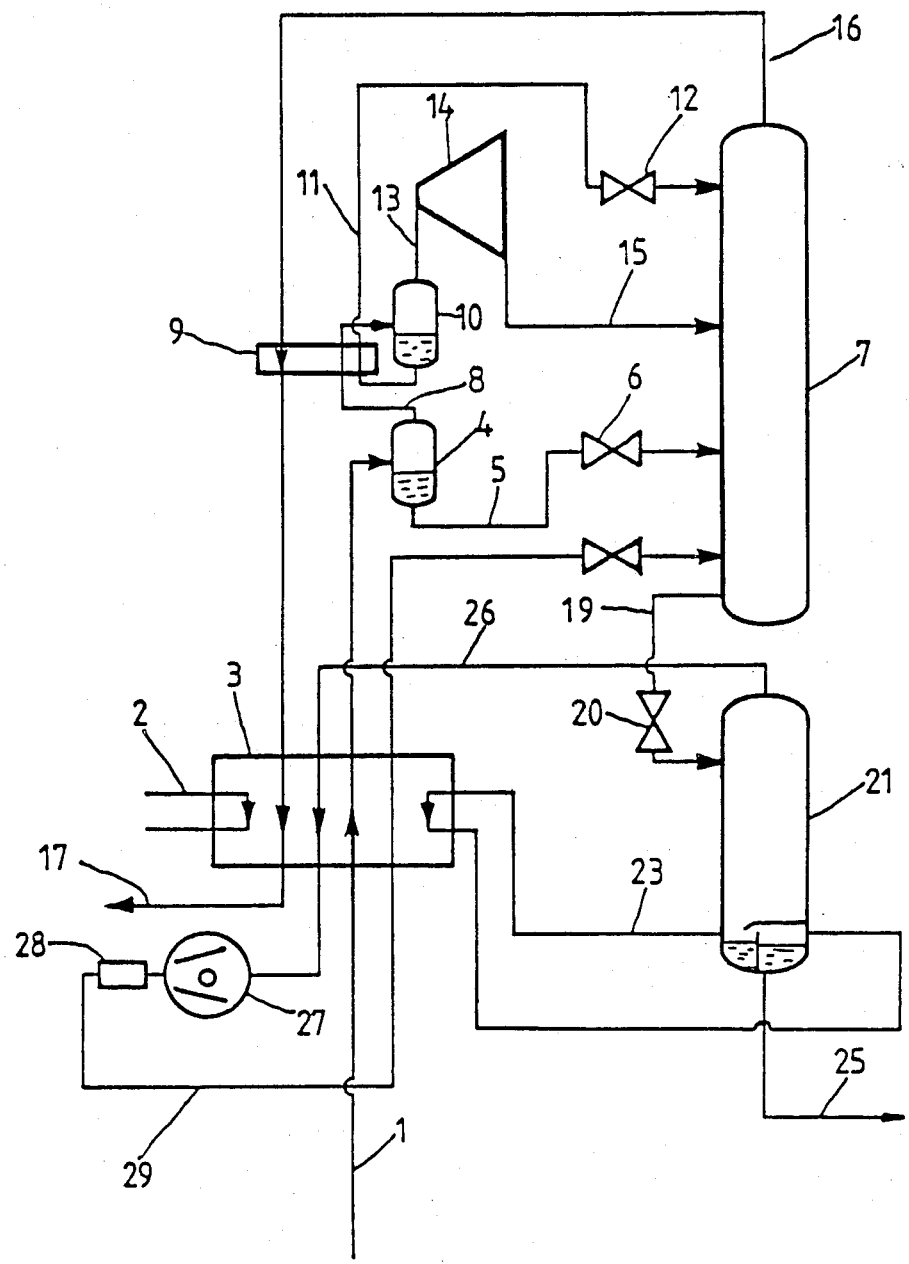
FIG. 2 is a flowsheet of a preferred modification of the process of FIG. 1.

FIG. 2 is a modification of the operation of the process shown in FIG. 1, affording an additional energy saving advantage. This version of the process provides that the condensate obtained in separator 10 is first subcooled in heat exchanger 9 to a temperature slightly above column 7 top temperature and then, after pressure reduction in valve 12, is introduced into the rectifying column 7 as a vapour-liquid mixture with about 10% vapour phase. In this procedure, the pressure-reduced, subcooled condensate yields the peak cold and is fed into column 7 above the gaseous phase passed into the column in conduit 15, the latter being derived from separator 10 and expansion turbine 14. For reasons of clarity, the intermediate heaters for rectifying columns 7 and 21 are not illustrated in FIG. 2. The conduits 29 and 23 are passed through heat exchanger 3.

Figure 3:
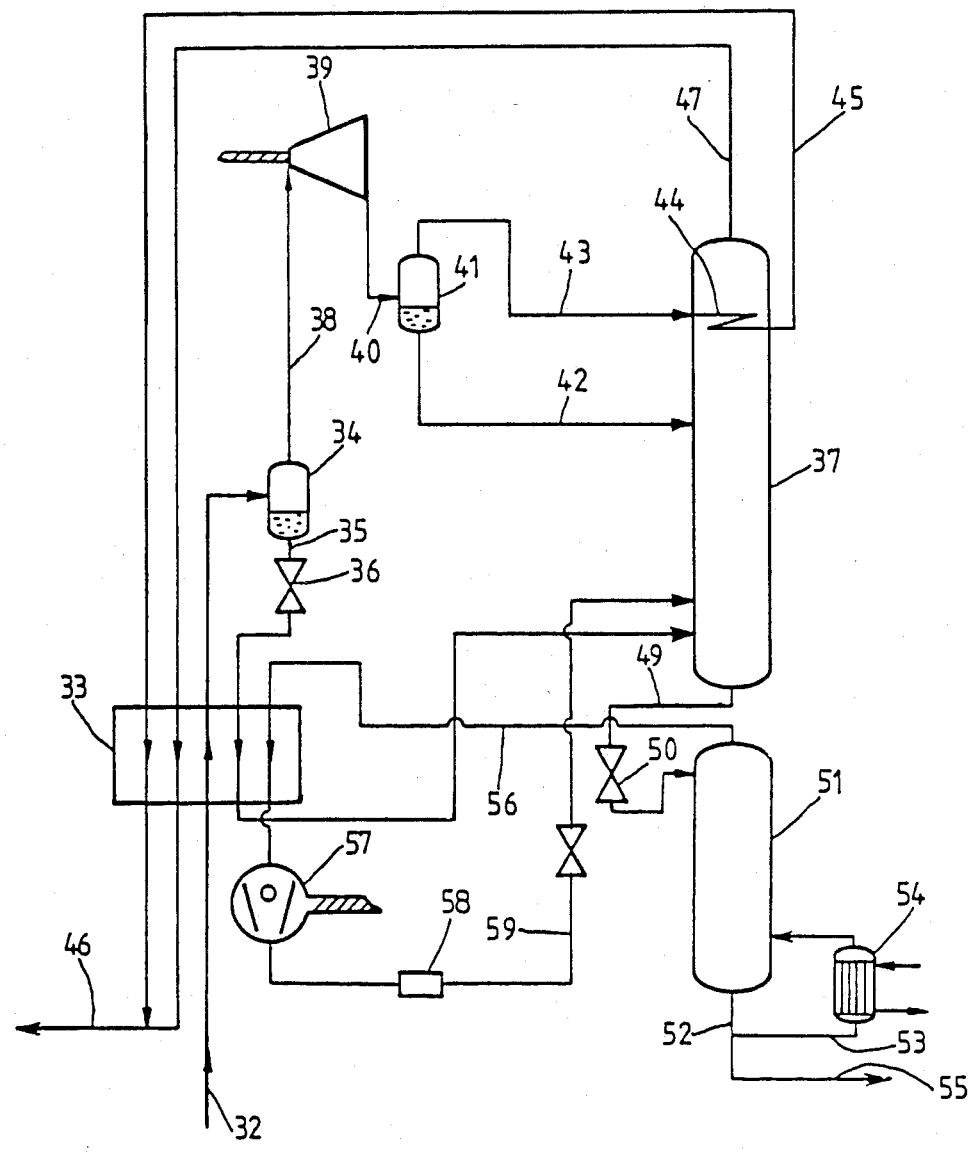
FIG. 3 is a process flowsheet of a preferred embodiment for separating $C_{3+}$ hydrocarbons from a crude gas stream.

In the embodiment shown in FIG. 3, relating to the separation of a $C_{3+}$ fraction from natural gas, a natural gas containing, 82.4 mol-% methane, 6.1 mol-% ethane, 3 mol-% propane, 2.7 mol-% $C_{4+}$ hydrocarbons, 4.9 mol-% carbon dioxide, 0.8 mol-% nitrogen and 0.1 mol-% hydrogen sulfide, is supplied via conduit 32 under a pressure of 75 bar and at a temperature of 322° K. In an indirect heat exchanger 33, cooled by process streams to be heated, the natural gas is cooled down to 229.5° K. During this step, components consisting essentially of the higher hydrocarbons contained in the natural gas are condensed, then separated in the downstream phase separator 34, withdrawn via a conduit 35, and expanded in valve 36 to the pressure of rectifying column 37. After being heated in heat exchanger 33 against natural gas to be cooled, the expanded, heated condensate is fed into the lower region of a first rectifying column 37.

Conversely, the uncondensed proportion of the natural gas is withdrawn from separator 34 via conduit 38 and engine-expanded in a turbine 39. The natural gas engine-expanded essentially to the pressure of the rectifying column 37, is discharged via conduit 40 and subjected to phase separation in a condensate separator 41. The liquid phase from separator 41 is introduced via conduit 42 into the middle zone of rectifying column 37 while the gaseous phase from separator 41 is passed via conduit 43 into a head condenser 44 of rectifying column 37 where this fraction, containing at this point essentially only methane, yields peak cold by indirect heat exchange. Subsequently, this fraction passes via conduit 45 into heat exchanger 33, is heated therein, and is finally discharged as product stream via conduit 46.

The components of the natural gas boiling more readily than $C_3$ hydrocarbons are obtained from the gas space of condensate separator 41 as well as at the head of rectifying column 37. Column 37, operated under a pressure of 32 bar, has a head temperature of 220° K. and a sump temperature of 286° K. The overhead product is discharged via conduit 47, heated in heat exchanger 33 and then mixed with the gaseous fraction from separator 41 withdrawn via conduit 45. The gaseous fraction withdrawn via conduit 46 consists, after the mixing step, of 87.3 mol-% methane, 6.4 mol-% ethane, 0.2 mol-% $C_{3+}$ hydrocarbons, 5.2 mol-% carbon dioxide, 0.8 mol-% nitrogen and 0.1 mol-% hydrogen sulfide. This product stream is obtained at a temperature of 319.4° K. and a pressure of 31.8 bar.

At a temperature of 286° K., a liquid is obtained in the sump of rectifying column 37 which contains minor amounts of components of greater volatility than $C_3$ hydrocarbons. The bottom liquid sump is discharged by way of conduit 49, expanded in valve 50 to 10 bar, and fed into a second rectifying column 51 operated under this pressure.

The rectifying column 51, operated at temperatures of between 278° K. at the head and 320° K. in the sump, separates the remaining, light components obtained from the sump product of rectifying column 37 from the $C_{3+}$ hydrocarbons to be obtained. As compared with a single-stage rectification, this version of the process, besides exhibiting the advantage that an overhead product of a relatively high pressure is obtained in column 37, has an additional, important advantage in that the bottoms product of column 51 can be obtained at sufficiently low temperatures that the thus-produced $C_{3+}$ hydrocarbons can be stored without special recooling. The advantageous temperature condition in the sump of column 51 also makes it possible to save substantial amounts of heating medium and permits simple expedients for heating the sump liquid, which can be done, for example, by hot water. For this purpose, a partial stream is branched off via conduit 53 from the bottoms product, withdrawn via conduit 52, heated in the hot water heat exchanger 54, and recycled into the column 51. The $C_{3+}$ fraction withdrawn via conduit 55 contains merely 0.78 mol-% lighter components, namely 0.76 mol-% ethane and 0.02 mol-% hydrogen sulfide. The content of heavier components in this fraction is 50.9 mol-% propane and 48.32 mol-% higher hydrocarbons.

From the head of column 51 is obtained an overhead fraction containing the light components that have passed into column 51, this fraction being discharged via conduit 56. After being heated in heat exchanger 33 against natural gas to be cooled, this fraction is compressed in compressor 57, (the latter being drivable, for example, by the energy obtained in turbine 39) then recooled to ambient temperature in recooler 58, and finally introduced via conduit 59 into the lower region of rectifying column 37.

In this process, the product streams comprise: in conduit 46, a gaseous fraction under a pressure of 31.7 bar and at a temperature of 319° K., and, in conduit 55, a stream containing $C_{3+}$ hydrocarbons under a pressure of 10 bar and at a temperature of 320° K.

The energy savings of the process of this invention with respect to the power requirement for the generation of external refrigeration during $C_{2+}$ separation from the natural gas, (embodiment of FIG. 1) are to be compared to the operation of the process proposed in the earlier U.S. patent application No. 650,016. In this older patent application, an electrical power requirement of 0.72 MW is required for generating the external cold. In the process of this invention according to FIG. 1, this power requirement is reduced to 0.53 MW and, with the preferred embodiment according to FIG. 2, this requirement is further decreased to 0.24 MW.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of $C_{2+}$ or $C_{3+}$ hydrocarbons from a hydrocarbon-containing raw gas under pressure, by recitification wherein the raw gas is cooled and expanded and the resultant condensates are introduced into a rectification column wherein the $C_{2+}$ or $C_{3+}$ hydrocarbons, respectively, are separated from the lower-boiling components, the improvement which comprises feeding the condensate fractions produced during cooling and expansion of the raw gas into a first rectifying column operated under a higher pressure to yield a bottoms fraction and an overhead product, the latter containing components boiling lower than the $C_{2+}$ or $C_{3+}$ hydrocarbons, expanding the bottoms fraction and then feeding resultant expanded bottoms fraction into a second rectifying column operating under a lower pressure than the first column, to yield $C_{2+}$ or $C_{3+}$ hydrocarbons bottoms product and an overhead fraction, compressing the latter overhead fraction and recycling resultant compressed overhead fraction into the first rectifying column.

2. A process according to claim 1, wherein the overhead fraction of the second rectifying column is heated prior to being compressed, and is recooled prior to being recycled into the first rectifying column.

3. A process according to claim 2, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

4. A process according to claim 1, wherein overhead fraction of the second rectifying column after being compressed, is passed into the raw gas to be cooled.

5. A process according to claim 4, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

6. A process according to claim 1, wherein the overhead fraction of the second rectifying column, after being compressed, is cooled and then passed into cooled raw gas from which condensate has been separated.

7. A process according to claim 6, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

8. A process according to claim 1, wherein components boiling below $C_{2+}$ or $C_{3+}$ are discharged from the process under pressure and wherein the first rectifying column is operated at a pressure above the discharge pressure.

9. A process according to claim 8, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

10. A process according to claim 1, wherein the first rectifying column is operated under a pressure of between 20 and 40 bar.

11. A process according to claim 10, wherein the second rectifying column is operated under a pressure of between 8 and 25 bar, with the operating pressure of the first rectifying column being at least 5 bar above the operating pressure of the second recitfying column.

12. A process according to claim 11, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

13. A process according to claim 10, wherein the second rectifying column is operated under a pressure of between 10 and 18 bar, with the operating pressure of the first rectifying column being at least 5 bar above the operating pressure of the second rectifying column.

14. A process according to claim 13, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

15. A process according to claim 10, wherein the second rectifying column is operated under a pressure of between 10 and 18 bar, with the operating pressure of the first rectifying column being at least 5 bar above the operating pressure of the second rectifying column.

16. A process according to claim 15, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

17. A process according to claim 10, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

18. A process according to claim 1, wherein the second rectifying column is operated under a pressure of between 8 and 25 bar, with the operating pressure of the first rectifying column being at least 5 bar above the operating pressure of the second rectifying column.

19. A process according to claim 18, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

20. A process according to claim 1, said raw gas being subjected to multistage cooling comprising a first cooling stage, separating a first condensate, introducing said first condensate to the first rectifying column, cooling the uncondensed proportion in a second cooling stage, separating a second condensate, subcooling resultant second condensate, feeding the subcooled second condensate into the upper zone of the first rectifying column, engine-expanding uncondensed gas from said second cooling stage, and passing resultant cooled engine-expanded gas into a zone of the first rectifying column below the feed point of the subcooled second condensate.

21. A process according to claim 1, wherein $C_{2+}$ hydrocarbons are being separated.

22. A process according to claim 1 wherein the temperature levels at the top and bottom of the second rectifying column are between 230° and 300° K.

* * * * *